United States Patent [19]

Trumbetas et al.

[11] Patent Number: 5,409,716
[45] Date of Patent: Apr. 25, 1995

[54] ENZYMATIC PROTEIN PROCESS

[75] Inventors: Jerome F. Trumbetas, Tarrytown; Roger W. Franzen, Pleasantville; Jimbay P. Loh, Peekskill, all of N.Y.

[73] Assignee: Kraft Foods, Inc., Northfield, Ill.

[21] Appl. No.: 79,690

[22] Filed: Jun. 18, 1993

Related U.S. Application Data

[63] Continuation of Ser. No. 889,653, May 27, 1992, abandoned.

[51] Int. Cl.⁶ ................................................ A23J 1/00
[52] U.S. Cl. ........................................ 426/7; 426/34; 426/35; 426/46; 426/656
[58] Field of Search .................... 426/7, 32, 34, 35, 41, 426/42, 44, 46, 49, 52, 656, 657

[56] References Cited

U.S. PATENT DOCUMENTS

| | | | |
|---|---|---|---|
| 3,896,241 | 7/1975 | Malaspina et al. | 426/271 |
| 3,974,294 | 8/1976 | Schwille et al. | 426/35 |
| 4,235,937 | 11/1980 | Remer | 426/534 |
| 4,293,571 | 10/1981 | Olofsson et al. | 426/657 |
| 4,293,583 | 10/1981 | Farr et al. | 426/657 |
| 4,313,962 | 2/1982 | Kim et al. | 426/35 |
| 4,734,287 | 3/1988 | Singer et al. | 426/41 |
| 4,853,232 | 8/1989 | Subramaniam et al. | 426/35 |
| 4,918,008 | 4/1990 | Gauri | 435/68.1 |

FOREIGN PATENT DOCUMENTS 0423958 1/1992 Japan .
2020667 11/1979 United Kingdom .

Primary Examiner—Donald E. Czaja
Assistant Examiner—Leslie Wong
Attorney, Agent, or Firm—Thomas A. Marcoux; Linn I. Grim; Thomas R. Savoie

[57] ABSTRACT

Enzymatic protein process removing objectionable odor and offensive taste from natural proteins and the bland, odor-free products produced thereby.

7 Claims, No Drawings

ENZYMATIC PROTEIN PROCESS

This application is a continuation of application Ser. No. 07/889,653, filed May 27, 1992 now abandoned.

This invention relates to a process of removing objectionable odor and offensive taste from natural proteins and the bland, odor-free products produced thereby.

BACKGROUND OF THE INVENTION

Among the sources of protein occurring naturally are milk and soybeans, both of which are quite abundant and readily processed to obtain useful proteins for human consumption.

However, one of the serious drawbacks to the use of these natural proteins, particularly in food products, is the objectionable odor and offensive taste which militate against the use of these proteins at any reasonable levels due to the aforesaid organoleptic problems. Because of these organoleptic problems, only limited use of these proteins has been possible in the food industry.

As is well known, milk protein is comprised of caseins and whey proteins. Whey is the serum remaining after removal of fat and casein from milk, the whey proteins including lactalbumin as well as lactoglobulin and other proteins. The component proteins are separated from the whey protein by known methods. The soybean proteins are obtainable from the residues produced after removal of soybean oil from soybeans. The protein is characterized by a beany flavor which limits its use thereof. Many attempts have been made to improve the organoleptic properties of these natural proteins including denaturation, ion-exchange treatment, the use of salt additives and high-shear treatment but these have been found wanting.

Whey proteins have been subjected to denaturation and centrifugation or ultra-filtration as described, for example, in U.K. Specification No. 2,020,667; ultra-filtration to concentrate whey solutions as described in U.S. Pat. No. 3,896,241; and subjecting whey protein to blending shear forces in the presence of a metal gluconate salt at a temperature below the denaturation temperatures of the whey proteins, as described in U.S. Pat. No. 4,235,937. In U.S. Pat. No. 4,218,490 there is disclosed a process for making a foodstuff employing a proteinaceous additive derived from a variety of sources including soy, blood, whey and oil seeds by ion-exchange treatment and spray drying techniques. Soluble whey lactalbumen employed in the additive is only at low levels. U.S. Pat. No. 4,734,287 describes a proteinaceous, water-dispersible colloid composed of non-aggregated particles of sweet whey protein having a dry means particle size of from about 0.1 to about 2.0 microns which is prepared by subjecting undenatured whey protein or concentrates thereof to a high shear treatment in an aqueous medium at a highly acid pH in the presence of aggregate blocking agents. The product, when hydrated is indicated to have desirable organoleptic properties normally attributable to fat/water emulsions.

U.S. Pat. No. 4,918,008 is directed to a process of hydrolyzing proteins, including lactalbumin, to produce products which are useful for pharmaceutical products. The process involves treating the selected protein with a protease, optionally in the presence of a lipase only if the starting material contains appreciable amounts of fat.

Milk or cheese whey protein, including the component proteins of whey protein, are known to contain significant amounts of fat which cannot be removed by simple solvent extraction, suggesting that the fat is somehow bound to the protein. The off-taste and objectionable odor of whey protein is presumably attributed to deterioration of the fat molecules, for example, by oxidation of ethylenic bonds in the unsaturated fatty acid chain of the fat molecule. Protein containing soybean fiber also contains similar contaminants which are responsible for the objectionable off-taste.

While the aforesaid prior art processes can result in whey protein products of reasonable organoleptic properties, these products develop off-taste and objectionable odors in relatively short periods of time on storage. In a matter of a few days, they can develop these undesirable properties which render them unfit for commercial use as, for example, human protein supplement or other use in foods intended for human consumption.

In contrast, the present process yields bland, odor-free natural protein which remains bland and odor-free over protracted periods of dry storage, for at least periods of 3 months and for up to 6 months and even one year and longer.

SUMMARY OF THE INVENTION

The starting natural protein is one which contains amounts of fat that are not readily removable by usual methods of extraction, i.e., the fat molecules are bound to the protein, and the protein is not organoleptically-acceptable for use in the food industry due to the presence of fat, the deterioration of which is responsible for objectionable odors and offensive taste. A variety of naturally-occurring proteins in this category can be treated in accordance with the present process to produce protein products which are organoleptically acceptable. Inclusive of the said proteins are milk and cheese whey protein and the individual components of whey, such as lactalbumin, beta lactoglobulin, serum albumin and various immunoglobulins, and soybean fiber containing soy protein. These proteins are preferably denatured prior to use in the present process. Denaturation of proteins is a well-known procedure and need not be elaborated for the purpose of this disclosure. In general, heat denaturation is used wherein the protein is subjected to heat to uncoil the protein molecules.

The process of this invention is accomplished by contacting the denatured natural protein with lipase in an aqueous medium, separating the thus-treated protein and removing free fatty acids from the separated protein. Removal of the hydrolyzed free fatty acids can be accomplished by solvent extraction using organic solvents, preferably food-acceptable organic solvents such as ethanol or exhaustive extraction using hot water and/or steam as solvent. Further, the fatty acids can be formed into soaps, preferably by adjusting the pH to 7 or higher and then water-washing will remove the soaps. Other extractive methods will occur to those skilled in the art. As should be apparent, the solvent selected should not be a solvent for the protein and should be inert to the protein.

This process is advantageously carried out at elevated temperatures usually from about 80° F. to about 140° F. and preferably from about 120° F. to about 140° F. In actuality, temperatures up to the denaturation temperature of the lipase enzyme can be used and this of course will vary with the lipase enzyme employed. The time of heating can vary considerably, but for the most part, heating for a period of about one to about three hours does suffice to produce a product of long dry-storage stability.

The lipase employed in the present process can be any of a wide variety of such enzymes and is not of itself critical. The lipase should be free of other enzymes which can adversely affect the outcome of the process. Thus, the lipase employed should be substantially free of protease, the enzyme which hydrolyzes proteins, as is well-known. Of course, trace amounts, possibly as contaminant depending on the source of the enzyme, can be present in the lipase employed without serious drawback. The amount of lipase used in the present process will usually range from about 0.05 to about 0.15 percent of the protein weight. In enzymatic reactions employing natural products, care often must be taken to prevent bacterial contamination of the reaction mixture. Bacterial contamination of the enzymatic reaction mixture can be avoided using well-known classical techniques. One such technique is to employ bacteria free natural protein as the substrate. Alternatively, the reaction mixture containing the protein can be pasteurized by heating prior to enzyme addition. When permitted, anti-bacterial agents can be added to the reaction mixture. Other precautionary measures are known to those skilled in the art.

After heating with the lipase is complete, the protein is separated from the aqueous hydrolysis medium and then the hydrolyzed fat moieties are removed, e.g., fatty acids hydrolyzed by the lipase as previously described. The method of removal of the fatty acids can be repeated as often as needed to assure efficient removal of the moieties responsible for off-taste and objectionable odor.

The product of the present new process is bland, odor free natural denatured protein which can be used at any desired level in food as a protein source. Of course, mixtures of the protein products produced by the present process can also be used in food products. Additionally, the present new products can be used as an opacifier for various food products such as beverages, cheese and mayonnaise. Since it is a whitening agent, it can be used in place of titanium dioxide which is commonly used in present day foods.

The following Examples further illustrate the invention. In the following Examples, the invention is illustrated with denatured whey protein also known as denatured lactalbumin in the trade. It should be understood that denatured soybean protein can be treated in substantially the same manner to produce a dry-storage stable product. Other protein-containing fibers such as corn, oat, wheat and the like will provide similar results.

EXAMPLE 1

Lipase, 0.6 g, was added to a mixture of 700 g of denatured milk whey protein in 2000 ml water and the mixture heated at 110° F. with stirring for one hour, after which it was cooled. The protein settled out and was separated from the cooled mixture. The cake was washed three times with 100 ml ethyl alcohol and then air dried. The product exhibited bland, odor-free organoleptic properties.

An alternative procedure for removal of fatty acids from the lactalbumin cake involves adjusting the pH of an aqueous suspension of the cake to pH=7 and then washing the cake with water to remove the soap formed.

A further alternative involves washing the separated lactalbumin cake with hot water to remove the fatty acids.

The lipase employed in this Example was obtained from Genencore, Inc., Experimental Code #031385 114/41 Code #1139. The whey protein was obtained from New Zealand Milk Products, Alatal 825.

EXAMPLE 2

Five 30 g samples of denatured whey protein (Alatal 825, New Zealand Milk Products) were added to 170 ml of water and/or NaOH as shown in Table 1. Samples 1 and 2 received no NaOH while NaOH was added to samples 3, 4 and 5 adjusted to insure constant solids to liquid ratio. Sample 1 served as control (no enzyme was added). To each of the remaining samples, 0.024 g of lipase (Genencore, 3TBU Lipase) was added and the samples were stirred for 2.5 hours at about 120° F. (actual temperatures for each sample are recorded in Table 1).

The samples were then cooled to refrigerator temperature and stored overnight at 40° F. The pH of each sample was recorded. The temperatures (about 120° F.) were reestablished and water and/or NaOH was added to insure constant solid to liquid ratios and to attain a pH of about 7. Samples were then centrifuged at 4000 rpm for 45 minutes.

Twenty ml supernatants from each sample were then submitted to Fatty Acid Methyl Ester (FAME) Gas Liquid chromatography analysis and the results are recorded in Table 2. From this Table, it can be seen that the higher the initial pH, the more free fatty acid is removed.

The cake from each sample was frozen with dry ice and freeze-dried overnight. Two grams of each sample were stored for fifteen days at 60° in sealed vials.

Organoleptically, sample 1 (the control) was the only obnoxious sample.

TABLE 1

| Samples | 1 | 2 | 3 | 4 | 5 |
|---|---|---|---|---|---|
|  | control |  |  |  | * |
| Enzyme | 0.00 | 0.024 g | 0.024g | 0.024 g | 0.024 g |
| NaOH (0.1N) | 0.00 | 0.00 | 3.60 | 7.20 | 10.00 |
| Water | 170.00 g | 170.00 g | 166.40 g | 159.20 g | 159.20 g |
| Whey Protein | 30.00 g | 30.00 g | 30.00 g | 30.00 g | 30.00 g |
| pH (Initial) | 4.32 | 4.33 | 5.82 | 6.45 | 6.80 |
| pH (Final) | 4.36 | 4.39 | 5.80 | 6.42 | 6.79 |
| Temp °F. | 119.70 | 119.10 | 118.60 | 118.30 | 117.90 |
| Added NaOH (0.1 N) | 10.00 g | 10.00 g | 6.40 g | 2.80 g | 0.00 g |
| Added Water | 0.00 | 0.00 | 3.60 g | 7.20 g | 10.00 g |
| pH | 7.45 | 7.52 | 7.34 | 7.19 | 6.94 |

For FAME analysis, the 20 ml supernatant samples were treated with 0.67 ml of 1N HCl. Soluble protein precipitated from the solution. The fatty acids were extracted with diethyl ether and analyzed.

TABLE 2

| Sample | pH | Solvent Peak | IS Peak | mg Fatty Acid (Corrected) |
|---|---|---|---|---|
| 1 | 4.36 | 28.98 | 45.41 | 50.75 |
| 2 | 4.39 | 6.26 | 60.77 | 48.82 |
| 3 | 5.80 | 23.93 | 33.02 | 117.34 |
| 4 | 6.42 | 35.37 | 25.82 | 132.58 |

TABLE 2-continued

| Sample | pH | Solvent Peak | IS Peak | mg Fatty Acid (Corrected) |
|---|---|---|---|---|
| 5 | 6.79 | 19.92 | 19.97 | 254.68 |

When samples of the treated denatured whey protein produced according to the foregoing Examples are tested for dry-storage stability, they show no appreciable offensive odor or off-taste for at least three months. Some samples are stable for at least 12 months. Stability determinations were made using measurement of hexanal which is a by-product of fatty acid oxidation and assumed to be responsible for off-taste and odor of whey protein. These measurements were accomplished using a Perkin-Elmer (HS-6) headspacer analyzer. The sample is weighed into a special meal containing an internal standard (usually 5 ppm 4-heptanone) and is sealed and heated at a preset temperature in the analyzer head. After a specific time interval (usually 15 minutes) the analyzer carousel assembly is pushed into the inject mode which causes the analyzer to aliquot a reproducible amount of headspace and inject into a column a gas chromatograph. Lipase-treated samples showed substantially less offensive levels than that of the untreated control.

EXAMPLE 3

A 20% aqueous mixture of denatured whey protein is heated to 115° F. for four hours with stirring in the presence of 0.2% lipase. This mixture is freeze-dried and then extracted extensively with hot ethanol. Methyl esters are prepared from the extract and analyzed for fatty acid composition.

The resulting filter cake is dispersed in water (20% mixture) and heated to 115° F. for four hours in the presence of 0.02% bromelin, a protease. This mixture is freeze-dried and extracted extensively with hot ethanol. As in the previous sample, methyl esters are prepared and the fatty acid profiles of the two samples are compared, as shown in Table 3.

The fatty acids are grouped together (Table 4) to show fatty acid comparisons between the lipase treated ethanol wash and the protease-treated filter cake wash. If random complexing of the fatty acids to the proteins occurs, the fatty acid profiles of each sample will be similar. As is obvious, the lipase treated wash demonstrates an increase of medium chain, long chain saturated and tri-unsaturated, while showing a decrease in mono- and di-unsaturated fatty acids.

In the following tables the unsaturation in the indicated fatty acids is of course ethylenic unsaturation. For brevity, the fatty acids are identified by the number of carbons and ethylenic bonds.

TABLE 3

| Fatty Acid (No. of Carbons: double bonds) | Percent | |
|---|---|---|
| | EtOH | Lipase Treatment |
| 4:0 | 0.26 | |
| 6:0 | 0.5 | |
| 8:0 | 0.61 | 1.13 |
| 10:0 | 1.58 | 2.41 |
| 12:0 | 2.39 | 3.45 |
| 14:0 | 9.68 | 10.99 |
| 14:1 | 1.24 | 0.28 |
| 15:0 | | 2.23 |
| 16:0 | 28.64 | 31.32 |
| 16:1 | 2.50 | 2.95 |
| 17:0 | 0.19 | |
| 17:0 | 0.89 | |
| 17:1 | 0.42 | 0.40 |
| 18:0 | 11.62 | 13.74 |
| 18:1 | 27.75 | 24.49 |
| 18:1 | 2.07 | 1.48 |
| 18:2 | 2.94 | 2.59 |
| 18:2 | 0.47 | 1.11 |
| 18:3 | 1.21 | 1.33 |
| 20:0 | 0.08 | 0.12 |
| ? | 0.92 | |
| ? | 3.96 | |
| | 100.00 | 100.00 |

TABLE 4

| | | EtOH Wash | Enzyme Treated EtOH Wash | Delta | Percent Reject |
|---|---|---|---|---|---|
| (a) | med ch | 5.42 | 6.99 | 1.57 | 28.94 |
| (b) | long ch | 41.43 | 47.40 | 5.97 | 14.42 |
| (c) | mono | 33.98 | 29.59 | −4.39 | −12.91 |
| (d) | di | 2.94 | 2.59 | −0.35 | −11.98 |
| (e) | tri | 1.21 | 1.33 | 0.12 | 10.09 |

(a) medium chain includes C4, C6, C8, C10, C12
(b) long chain is C14:0, C16:0, C18:0, C19:0, C:20:0, C22:0
(c) mono is C14:1, C16:1, C18:1, C20:1
(d) di is C16:2, C18:2, C20:2
(e) tri is C18:3

What is claimed is:

1. A process for preparing bland, odor-free denatured natural proteins which consists essentially of contacting the denatured protein with lipase which is substantially free of protease at a temperature from about 80° F. to about 140° F. and removing the hydrolysis products to obtain a bland, odor-free denatured natural protein selected from the group consisting of milk whey, cheese whey, lactalbumin, beta lactoglobulin, serum albumin, immunoglobulins and soybean protein wherein said protein in the dry state has no offensive odor or off-taste for a period of at least three (3) months.

2. The process according to claim 1 wherein from about 0.05 to about 0.15 percent of lipase is employed based on the protein weight.

3. The process according to claim 1 wherein the temperature is from about 120° F. to about 140° F.

4. The process according to claim 1 wherein said contacting is for a period of from about 1 to about 3 hours.

5. The process according to claim 1 wherein the protein is whey protein.

6. The process according to claim 1 wherein the protein is soybean protein.

7. The process according to claim 1 wherein the protein is lactalbumin.

* * * * *